(12) United States Patent
Statner et al.

(10) Patent No.: US 7,921,959 B2
(45) Date of Patent: Apr. 12, 2011

(54) STETHOSCOPE PROTECTIVE DEVICE

(75) Inventors: Barry Statner, Westlake Village, CA (US); Ashim Arora, Simi Valley, CA (US)

(73) Assignee: Steth-Glove, Inc., Westlake Village, CA (US)

( * ) Notice: Subject to any disclaimer, the term of this patent is extended or adjusted under 35 U.S.C. 154(b) by 0 days.

(21) Appl. No.: 12/567,546

(22) Filed: Sep. 25, 2009

(65) Prior Publication Data

US 2010/0032231 A1 Feb. 11, 2010

Related U.S. Application Data

(63) Continuation of application No. 11/670,372, filed on Feb. 1, 2007, now Pat. No. 7,614,477.

(60) Provisional application No. 60/766,672, filed on Feb. 3, 2006.

(51) Int. Cl.
*A61B 7/02* (2006.01)

(52) U.S. Cl. .......................................... 181/131; 383/60

(58) Field of Classification Search .................. 181/131; 383/60
See application file for complete search history.

(56) References Cited

U.S. PATENT DOCUMENTS

| | | | |
|---|---|---|---|
| 2,990,100 A * | 6/1961 | Randak | 383/43 |
| 3,262,632 A * | 7/1966 | Brady et al. | 229/123.3 |
| 4,406,346 A * | 9/1983 | Pope, Jr. | 181/131 |
| 5,069,261 A | 12/1991 | Ji | |
| 5,466,898 A | 11/1995 | Gilbert | |
| 5,623,131 A * | 4/1997 | Earnest | 181/131 |
| 6,006,856 A * | 12/1999 | Skubal et al. | 181/131 |
| 6,022,144 A | 2/2000 | Hausslein | |
| 6,594,872 B2 * | 7/2003 | Cisek | 24/401 |
| 7,036,190 B2 * | 5/2006 | Demarest | 24/401 |
| 7,614,477 B2 | 11/2009 | Statner et al. | |
| 2001/0026650 A1 * | 10/2001 | Denko | 383/60 |
| 2002/0170771 A1 * | 11/2002 | Milam et al. | 181/131 |
| 2004/0040869 A1 * | 3/2004 | Menceles | 206/37 |
| 2005/0204517 A1 * | 9/2005 | Demarest | 24/400 |
| 2007/0193822 A1 * | 8/2007 | Statner et al. | 181/131 |

OTHER PUBLICATIONS

Examination Report, dated Jun. 22, 2010, U.K. Application No. GB815886.7.

* cited by examiner

*Primary Examiner* — Elvin G Enad
*Assistant Examiner* — Forrest M Phillips
(74) *Attorney, Agent, or Firm* — Fitch Even Tabin & Flannery

(57) ABSTRACT

A stethoscope protective device is for easily and hygienically covering the head and at least a portion of the connector tube of a stethoscope. The device can be quickly applied to the stethoscope while eliminating or minimizing the need for contact by a patient of the head and connector tube during examination. In a single-handed operation, the stethoscope head and connector tube can be readily slipped into and secured within the protective device. The device is constructed at least in part of a material that is acoustically transmissive and provides a barrier for reducing the transmission of microorganisms.

17 Claims, 4 Drawing Sheets

STETHOSCOPE PROTECTIVE DEVICE

CROSS REFERENCE TO RELATED APPLICATIONS

This application claims priority from and is a continuation of U.S. application Ser. No. 11/670,372, filed Feb. 1, 2007, now U.S. Pat. No. 7,614,477 which claims priority from U.S. Provisional Application No. 60/766,672, filed Feb. 3, 2006, both of which such applications are incorporated herein by reference.

FIELD OF INVENTION

This relates to a device for inhibiting the transmission of microorganisms. In particular, this relates to a stethoscope cover that reduces the risk of stethoscope contamination by transmitting biohazards, including infectious microorganisms.

BACKGROUND

Disease-causing microorganisms are ubiquitous in healthcare environments. These locations include hospitals, outpatient clinics, ambulatory surgical centers, nursing homes, doctors' offices, etc. In these locations pathogenic microorganisms are frequently found on patients' skin and clothing as well as on other surfaces including beds, linens, and diagnostic and therapeutic medical equipment.

Stethoscopes are medical equipment that are known to transmit pathogenic agents from patient to patient. Unless a health care provider sterilizes the stethoscope between each examination, a subsequent patient can become contaminated with microorganisms that may have been present on a prior patient. However, it is believed that the great majority of health care providers do not clean or sanitize their stethoscopes between examinations of different patients. Therefore many stethoscopes can end up transmitting numerous types of often-harmful microorganisms between patients.

To address this problem, there are known devices for covering stethoscopes in an effort to provide barrier protection. However these known designs have significant drawbacks. For example some designs only cover the head of the stethoscope, and therefore the rest of it remains exposed to possible contamination. Other designs cover a larger portion of the stethoscope, but are awkward for the user to work with (including in some instances, the requirement for a two-handed operation), or alternatively are relatively complex and expensive in their construction. This latter disadvantage can be due to a complex shape of the cover which increases manufacturing costs or due to the need for separate, relatively expensive components for use with the cover. Yet other known designs employ adhesives to attach protective covers to stethoscope heads. This can result in the head becoming fouled with adhesive residue thus exacerbating the transmission problem, as this can cause the stethoscopes to retain and thereby transmit an even greater number of microorganisms.

While known devices are directed to the same general problem addressed in this disclosure, there remains a need for an inexpensive, effective and easily-operated means for inhibiting the transmission of microorganisms via stethoscopes. It does not appear that there has been a general acceptance by health care providers of any of the known devices. It is believed that this lack of acceptance is largely due to the relative high expense, the lack of effectiveness or the impracticality of operation of the devices.

Thus there exists a need for improved methods and devices for inhibiting the transmission of microorganisms via stethoscopes, having a low cost and a simple, fast operation.

SUMMARY OF THE ILLUSTRATED EMBODIMENTS

A disposable stethoscope protective device is provided that has a sleeve and a clasp connected to the sleeve. When applied over the head and connector tube of a stethoscope, the sleeve acts as a barrier to microorganisms, yet permits acoustic waves to transmit through the sleeve so that the stethoscope may be used in an examination. When applied before stethoscope use and discarded immediately thereafter, the device inhibits the transmission of potentially disease-causing microorganisms from patient to patient.

In one aspect, the device comprises an elongated sleeve defining an interior volume and having a closed first sleeve end and an opened second sleeve end defining a mouth. The sleeve is constructed of a material that is acoustically transmissive and generally impermeable to microorganisms and fluids. A clasp is fixedly attached to substantially all of the perimeter of the mouth of the second sleeve end. The clasp is configured to hold the second sleeve end mouth in a closed position when no external compressive force is applied to the clasp and to open the second sleeve end mouth when an external compressive force is applied to the clasp.

In another aspect, the stethoscope head has a head vertical length and the stethoscope connector tube has a connector tube length. The elongated sleeve has a sleeve length that falls between a first distance and a second distance, wherein the first distance is about equal to the sum of the head vertical length plus about one half of the connector tube length, and the second distance is about equal to the sum of the head vertical length plus the connector tube length.

In yet another aspect, the stethoscope connector tube has a connector tube cross-sectional thickness. The clasp comprises a resilient member formed into a generally closed-loop configuration and of sufficient size to approximately encircle the perimeter of the mouth of the second sleeve end. The clasp further comprises a first clasp side, a second clasp side, a first clasp end connecting the first and second clasp sides, and a second clasp end connecting the first and second clasp sides. When no external compressive force is applied to the first and second clasp ends, each of the first and second clasp sides has a generally elongated shape, and they either abut one another or are spaced apart by a first distance that is less than the connector tube cross-sectional thickness. However when an external compressive force is applied to the first and second clasp ends, each of the first and second clasp sides has a generally arcuate shape and at least a portion of the first and second clasp sides are spaced apart by a second distance that is greater than the connector tube cross-sectional thickness.

In an alternative embodiment of the invention, a method for inhibiting the transmission of microorganisms is disclosed. An external compressive force is applied to first and second clasp ends of a clasp that is fixedly attached to an elongated sleeve. The clasp comprises a first clasp side and a second clasp side, wherein the first clasp end connects the first and second clasp sides and the second clasp end connects the first and second clasp sides. A head of a stethoscope and at least a portion of a connector tube of the stethoscope are inserted into the elongated sleeve while the external compressive force is being applied to the first and second clasp ends. The external compressive force is released from the first and second clasp ends after the stethoscope head and the at least a portion of the connector tube are inserted into the elongated sleeve.

There are additional aspects to the present inventions. It should therefore be understood that the preceding is merely a brief summary of some embodiments and aspects of the present inventions. Additional embodiments and aspects are referenced below. It should further be understood that numerous changes to the disclosed embodiments can be made without departing from the spirit or scope of the inventions. The preceding summary therefore is not meant to limit the scope of the inventions. Rather, the scope of the inventions is to be determined by appended claims and their equivalents.

BRIEF DESCRIPTION OF THE DRAWINGS

These and/or other aspects and advantages of the present invention will become apparent and more readily appreciated from the following description of certain embodiments, taken in conjunction with the accompanying drawings of which.

DETAILED DESCRIPTION

Figure 1:
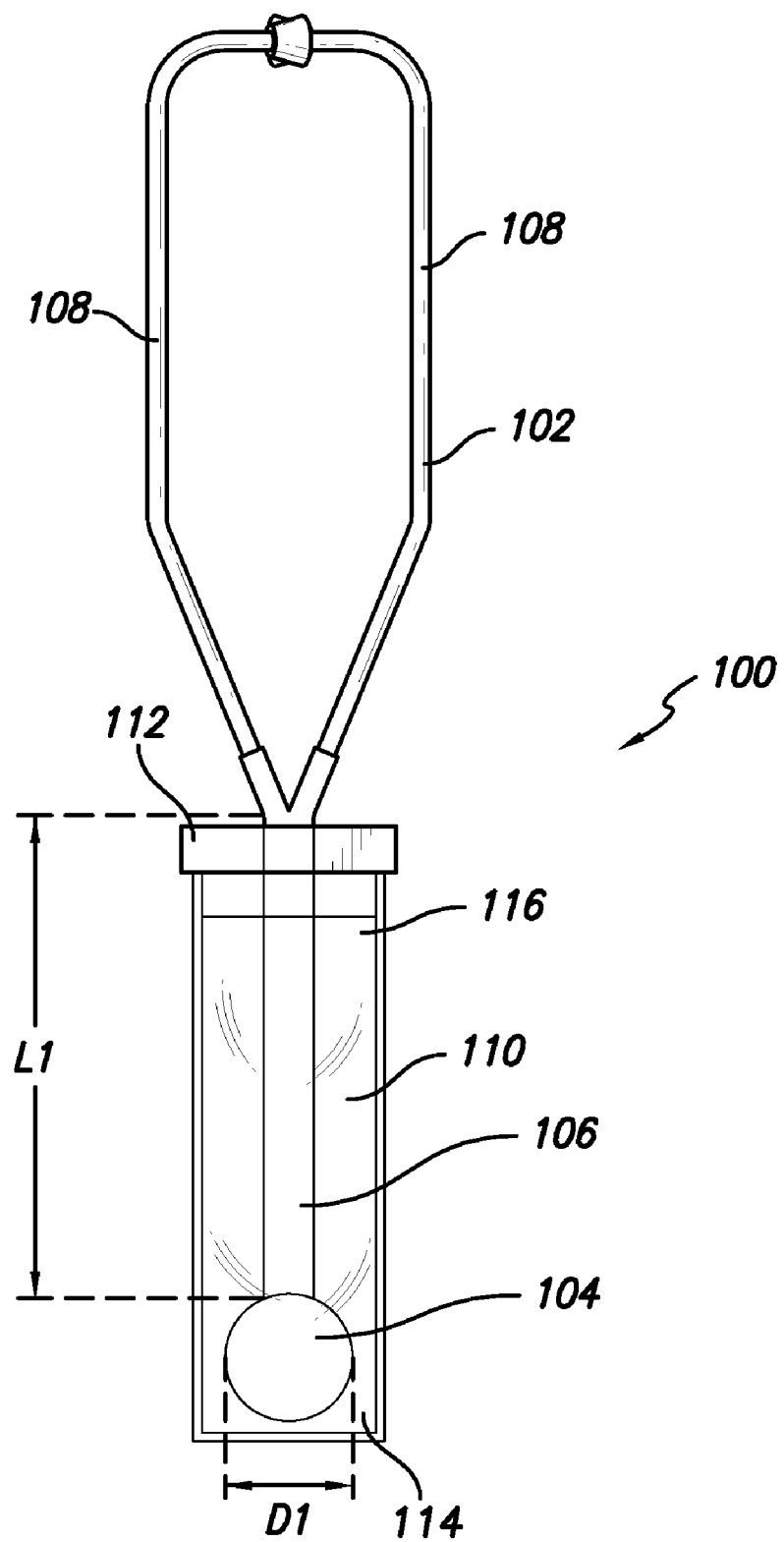
FIG. 1 is a front plan view of a stethoscope inserted into a stethoscope protective device.

The following description is of the best mode presently contemplated for carrying out the invention. Reference will be made in detail to embodiments of the present invention, examples of which are illustrated in the accompanying drawings, wherein like reference numerals refer to like elements throughout. It is understood that other embodiments may be used and structural and operational changes may be made without departing from the scope of the present invention.

The stethoscope protective devices disclosed herein are for easily and hygienically covering the heads and at least a portion of the connector tubes of stethoscopes. The devices can be quickly applied to the stethoscopes while eliminating or minimizing the need for contact by a patient of the heads and connector tubes during examination. In a single-handed operation the stethoscope head and connector tube can be readily slipped into and secured within the protective device which is made possible through the unique design of the devices themselves.

The devices comprise a material that is acoustically transmissive and provides a barrier for reducing the transmission of microorganisms. Preferably, the barrier reduces or eliminates the transmission of dirt, fluids, oils, etc., all of which may carry pathogenic microorganisms. The devices are designed for easy attachment to and removal from the stethoscopes so that this can be easily accomplished in a quick, single-handed operation.

Referring to FIG. 1, there is shown a stethoscope 102 that is partially inserted into a protective device 100 that is used for inhibiting the transmission of microorganisms via barrier protection. The stethoscope 102 has a head 104 (sometimes referred to in the art as a stethoscope bell), a connector tube 106 extending from the head 104, and two ear tubes 108 extending from the connector tube 106. The stethoscope head 104 has a head vertical length. As used herein, the head vertical length refers to the external dimension of a stethoscope head as measured in the direction of an imaginary line extending from the length of the connector tube when the connector tube is extended downwardly as shown in FIG. 1, i.e., when worn by a user but not in use by him/her for an examination. For example, for stethoscope heads having a generally circular shape such as the head of FIG. 1, the head vertical length would be the same as the head diameter D1 as shown in FIG. 1. However for example, for stethoscope heads having a generally elliptical shape with the major axis of the ellipse oriented vertically when the stethoscope is being worn, then the head vertical length would correspond to the length of the major axis of the ellipse.

The connector tube 106 has a connector tube length L1 and a connector tube cross-sectional thickness. As used herein, connector tube cross-sectional thickness refers to the distance by which a connector tube extends outwardly from the body or clothing of a user when the connector tube is extended downwardly as shown in FIG. 1, i.e., when worn by a user, but not in use by him/her for an examination. For example, for a connector tube having a generally circular cross-section, like the connector tube shown in FIG. 1, the connector tube cross-sectional thickness corresponds to the outer diameter of the tube. As another example, for connector tubes having an exterior profile that generally appears to be two tubes disposed in abutment to one another, the connector tube cross-sectional thickness would correspond to the outer diameter of one of the two tubes.

Figure 2:
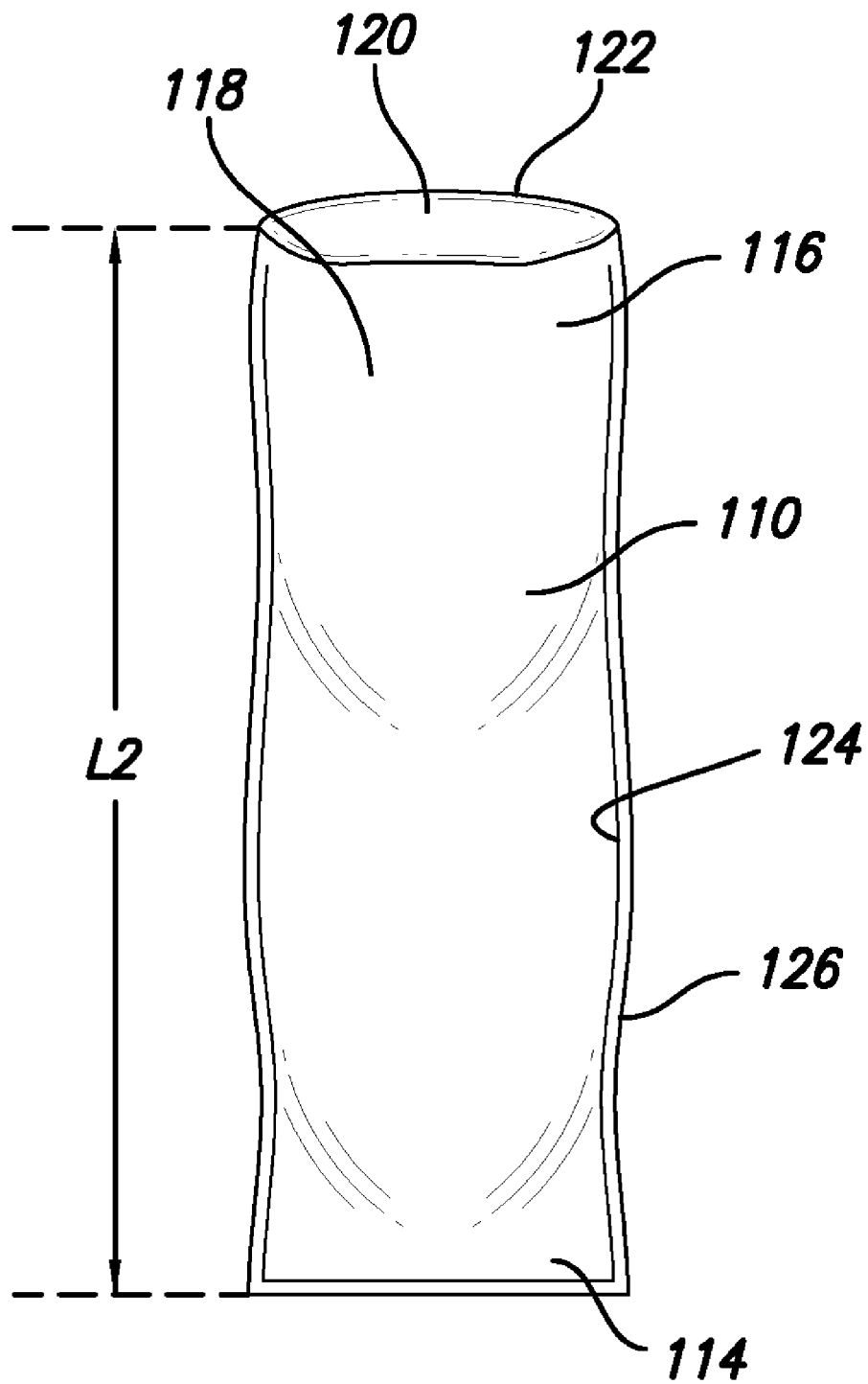
FIG. 2 is a front perspective view of the sleeve of the protective device of FIG. 1.

The protective device 100 comprises an elongated sleeve 110 and a clasp 112. Referring to FIG. 2, the sleeve 110 defines an interior volume 118 and has a closed first sleeve end 114 and an opened second sleeve end 116 defining a mouth 120 having a perimeter 122 and leading into the interior volume 118. The sleeve 110 provides a means for isolating a portion of the stethoscope 102 from microorganisms and is constructed of a material that is acoustically transmissive and generally impermeable to microorganisms and fluids. Such materials may include for example polyethylene or other thermoplastics, acetate, paper or cloth. In the illustrated embodiment, the sleeve 110 has an inner sleeve surface 124, an outer sleeve surface 126 and a thickness of about 0.002 inches. However other embodiments may employ other thicknesses as well so long as the material is acoustically transmissive and generally impermeable to microorganisms and fluids.

The sleeve 110 has a length L2 that is about equal to the sum of the head vertical length plus the connector tube length L1 so that the sleeve 110 can enclose the lower portion of the stethoscope 102 up to about the location where the ear tubes 108 connect with the connector tube 106. In other embodiments, however, the sleeve length can be shorter so that it at least covers the head 104 plus approximately the lower one half of the connector tube length L1. Thus in various embodiments of the invention, the sleeve length can vary and fall between a first distance corresponding to the sum of the head vertical length plus about one half of the connector tube length L1, and a second distance corresponding to the sum of the head vertical length plus about the connector tube length L1. In alternative embodiments, the sleeve length falls between about 10 inches and about 22 inches with a preferred embodiment having a sleeve length of about 18 inches. Such dimensions are likely to be suitable for both adult and pediatric stethoscopes and able to enclose these stethoscope heads and at least one half of these stethoscope connector tubes.

Although the embodiment of FIGS. 1 and 2 show a sleeve 110 having a generally rectangular shape, alternative embodiments can include other shapes, such as a square, tubular, trapezoidal, etc. The first sleeve end can be longer or shorter than the second sleeve end. The sides of the sleeve can have a concave shape, a convex shape or be straight or curved in other fashions.

Figure 6:
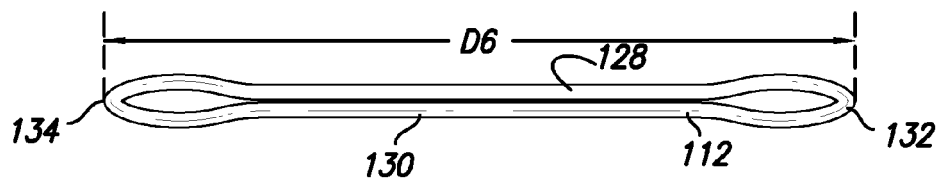
FIG. 6 is a top plan view of the clasp of FIG. 1 in the closed position.

The clasp 112 provides a means for removably securing the sleeve 110 to the stethoscope 102 during patient examination or other uses. The clasp 112 is comprised of a resilient member formed into a generally closed-loop configuration. The clasp 112 therefore permits the sleeve 110 to be removably secured to the stethoscope 102 during its use with a patient and also be readily removed from the stethoscope 102 at a later point in time. Referring to FIG. 6, the clasp 112 has a first clasp side 128, a second clasp side 130, a first clasp end 132 connecting one end of each of the first and second clasp sides 128, 130, and a second clasp end 134 connecting the opposite end of each of the first and second clasp sides 128, 130.

Figure 3:
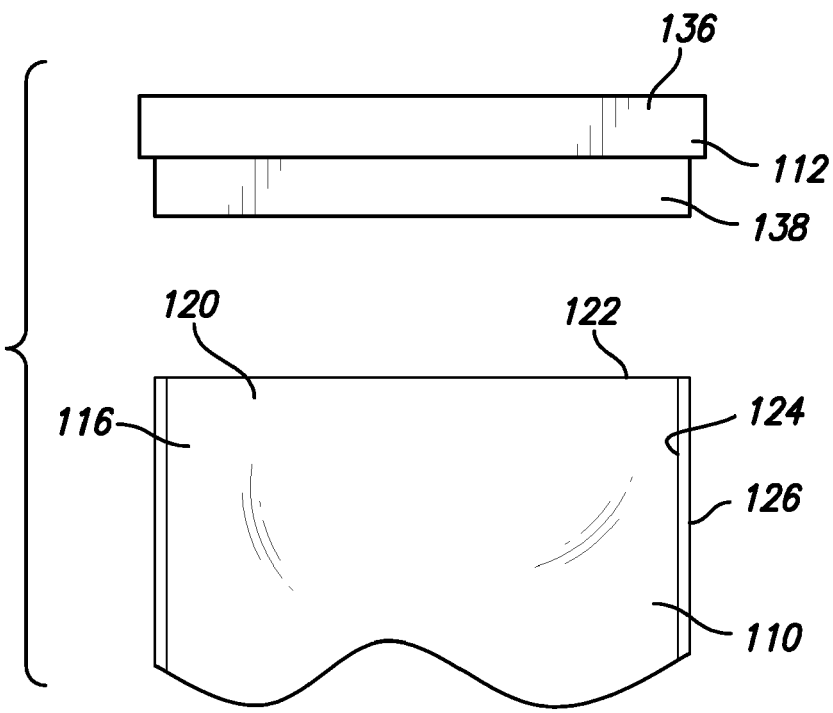
FIG. 3 is an exploded parts view of a clasp and a portion of the sleeve of the protective device of FIG. 1.
Figure 4:
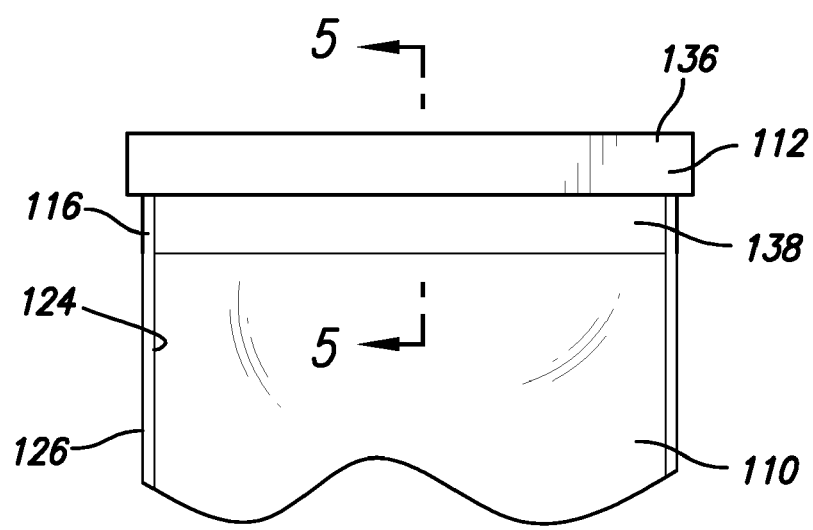
FIG. 4 is a front plan view of the clasp and a portion of the sleeve of the protective device of FIG. 1.
Figure 5:
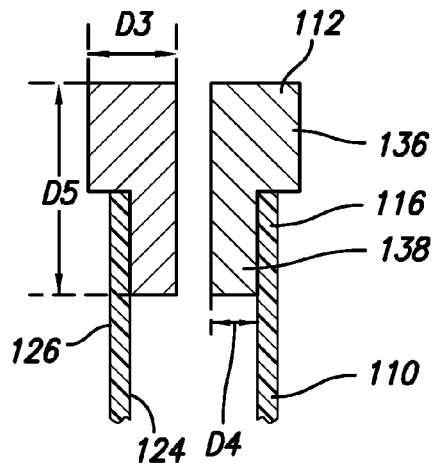
FIG. 5 is a cross-section view of the clasp and the sleeve as shown along lines 5-5 of FIG. 4.

Referring now to FIGS. 3, 4 and 5, the clasp 112 has an upper portion 136 having a first cross-sectional thickness D3 and a lower portion 138 having a second cross-sectional thickness D4 that is less than the first cross-sectional thickness D3. The overall clasp 112 is of sufficient size to approximately encircle the perimeter 122 of the mouth 120 of the second sleeve end 116, so that the clasp lower portion 138 is fixedly attached to substantially the entire perimeter 122 of the second sleeve end mouth 120. In the illustrated embodiment, the clasp lower portion 138 is attached to the inner sleeve surface 124 of the sleeve 110. However other embodiments may include other attachment methods and locations.

When in the closed position with no external compressive force applied to the clasp 112 as shown in FIG. 6, each of the first and second clasp sides 128, 130 has a generally elongated shape and abuts one another. Alternatively, each clasp side can be spaced apart by a relatively small distance that is less than the stethoscope connector tube cross-sectional thickness. Either way, the clasp 112 is constructed to grip the stethoscope connector tube 106 when the stethoscope 102 is inserted into the sleeve 110 and no external compressive force is applied to the clasp 112.

Figure 7:
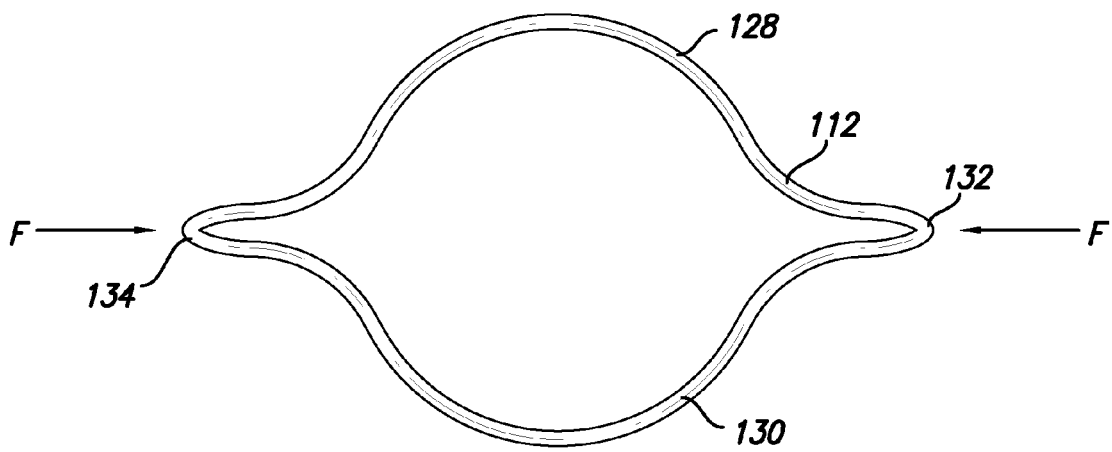
FIG. 7 is a top plan view of the clasp of FIG. 1 in the open position.

Referring to FIG. 7, when the user desires to open the clasp 112, the first and second clasp ends 132, 134 are squeezed together thus providing an external compressive force F that causes each of the first and second clasp sides 128, 130 to bend apart and form a generally arcuate shape thus opening the sleeve mouth 120. (FIG. 2) The first and second clasp sides 128, 130 are spaced apart by a distance that is greater than the connector tube cross-sectional thickness and the stethoscope head thickness for convenient insertion or removal of the stethoscope 102 into or from the sleeve 110. When the external compressive force F is removed, the first and second clasp sides 128, 130 come back together due to the resilient nature of the material from which the clasp 112 is constructed. Thus the clasp 112 will return to its closed position as shown in FIG. 6 if no stethoscope has been inserted. Alternatively if a stethoscope has been inserted, the material's resiliency will cause the first and second clasp sides 128, 130 to return to a nearly-closed position that will allow them to grip the stethoscope connector tube thus holding the sleeve in place.

In the illustrated embodiment, the clasp 112 has an overall length D6 of about 4.25 inches and an overall height D5 of about 0.5 inches. The clasp 112 is constructed of polypropylene, with the first cross-sectional thickness D3 being about 0.06 inches, and the second cross-sectional thickness D4 being about 0.03 inches. However other embodiments may be constructed of other resilient materials, such as for example, metals, metal alloys, thermoplastics, thermoplastic elastomers, rubber, cardboard, etc., and may have other cross-sectional profiles, including a uniform profile or profiles of different geometries and thicknesses. In yet other embodiments, the clasp may comprise other closure mechanisms including, for example, snaps, zip locks, Velcro®-type fasteners, and adhesive substances.

Figure 8:
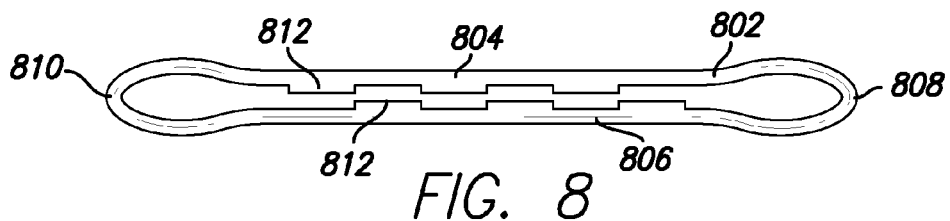
FIG. 8 is an alternative embodiment of a clasp for a stethoscope protective device.

FIG. 8 shows an alternative embodiment of a clasp 802 for attaching to a sleeve. This clasp 802 is essentially the same as the clasp 112 of FIGS. 1, 3-7, includes a first clasp side 804, a second clasp side 806, a first clasp end 808 and a second clasp end 810, and operates in generally the same manner. However in this embodiment each of the first and second clasp sides 804, 806 has a plurality of projections 812 extending inwardly and disposed in a mating relationship with one another when the clasp 802 is in the closed position s shown in FIG. 8. The projections 812 serve to enhance the grip of the clasp 802 on a stethoscope connector tube.

In use, a doctor or other health care provider having a stethoscope hanging from his/her neck grasps a clasp portion of a protective device with one hand and removes the device from a dispenser, box or other container having a plurality of such protective devices. Using the thumb and index finger of just one hand, a compressive force is applied to both ends of the clasp thereby opening the mouth of the protective device for a distance sufficient to allow insertion of the stethoscope head. The stethoscope head is inserted into the sleeve portion of the protective device along with at least a portion of the stethoscope connector tube while the compressive force is being applied to clasp ends.

Once the stethoscope head and connector tube are inserted in the sleeve, so that the head is at or near the closed end of the sleeve, the compressive force is released from the clasp ends thereby closing the mouth of the protective device and freeing the hand of the health care provider. The resiliency of the material from which the clasp is formed will cause it to grip the connector tube while the stethoscope is in use. This in turn will hold the sleeve in place so that it will form a barrier that is generally impermeable to microorganisms and fluids. Nevertheless, the sleeve is constructed of a material that also is acoustically transmissive thus permitting the health care provider to use the stethoscope for patient examination while inhibiting the transmission of microorganisms from the patient to the stethoscope and vice versa.

Once the examination is concluded, the steps described above are essentially reversed so that the stethoscope can be easily and quickly extracted from the protective device in a single-handed operation, and then the protective device can be discarded.

In view of the above, it will be appreciated that embodiments of the invention overcome many of the long-standing problems in the art by providing a stethoscope protective device for easily and hygienically covering the heads and at least a portion of the connector tubes of stethoscopes. The device can be quickly applied to the stethoscope while eliminating or minimizing the need for contact by a patient of the head and connector tube during examination. In a single-handed operation, the stethoscope head and connector tube can be readily slipped into and secured within the protective device. The device is constructed in part of a material that is acoustically transmissive and provides a barrier for reducing the transmission of microorganisms.

While the description above refers to particular embodiments of the present invention, it will be understood that many modifications may be made without departing from the spirit thereof. The claims are intended to cover such modifications as would fall within the true scope and spirit of the present invention. The presently disclosed embodiments are therefore to be considered in all respects as illustrative and not restrictive, the scope of the invention being indicated by the claims rather than the foregoing description, and all changes which come within the meaning and range of equivalency of the claims are therefore intended to be embraced therein.

What is claimed is:

1. An apparatus for use by a user having one hand and for use with a stethoscope having a stethoscope head and a connector tube extending from the stethoscope head, the apparatus comprising:
   an elongated sleeve constructed of a material that is acoustically transmissive and generally impermeable to microorganisms and fluids, wherein the elongated sleeve defines an interior volume and has a closed sleeve first end and an opened sleeve second end defining a mouth; and
   a clasp fixedly attached to the mouth of the elongated sleeve,
   wherein the clasp is configured to move from a closed position to an open position by an external compressive force applied to the clasp by the one hand of the user,
   wherein the clasp is further configured to close the mouth of the elongated sleeve when no external compressive force is applied to the clasp and to open the mouth of the elongated sleeve when the external compressive force is applied to the clasp, and
   wherein the clasp is further configured to grip the connector tube when the stethoscope head and at least a portion of the connector tube are disposed within the elongated sleeve and when no external compressive force is applied to the clasp.

2. The apparatus of claim 1 wherein the stethoscope head has a head vertical length and wherein the stethoscope connector tube has a connector tube length,
   wherein the elongated sleeve has a sleeve length that falls between a first distance and a second distance, wherein the first distance is about equal to the sum of the head vertical length plus about one half of the connector tube length, and wherein the second distance is about equal to the sum of the head vertical length plus the connector tube length.

3. The apparatus of claim 1 wherein the mouth has a perimeter, and wherein the clasp is fixedly attached to substantially all of the perimeter of the mouth.

4. The apparatus of claim 3 wherein the stethoscope connector tube has a connector tube cross-sectional thickness, wherein the clasp comprises a resilient member formed into a generally closed-loop configuration and of sufficient size to approximately encircle the perimeter of the mouth of the elongated sleeve,
   wherein the clasp further comprises a first clasp side, a second clasp side, a first clasp end connecting the first and second clasp sides, and a second clasp end connecting the first and second clasp sides,
   wherein when no external compressive force is applied to the first and second clasp ends, the first and second clasp sides are one of abutting one another and spaced apart by a first distance that is less than the connector tube cross-sectional thickness, and
   wherein when the external compressive force is applied to the first and second clasp ends, at least a portion of the first and second clasp sides are spaced apart by a second distance that is greater than the connector tube cross-sectional thickness.

5. The apparatus of claim 4 wherein each of the first and second clasp sides has a generally elongated shape when no external compressive force is applied to the first and second clasp ends, and a generally arcuate shape when the external compressive force is applied to the first and second clasp ends.

6. The apparatus of claim 5 wherein each of the first and second clasp sides has a plurality of projections extending inwardly and disposed in a mating relationship when no external compressive force is applied to the first and second clasp ends.

7. The apparatus of claim 4 wherein the clasp further comprises an upper portion having a first cross-sectional thickness and a lower portion having a second cross-sectional thickness that is less than the first cross-sectional thickness.

8. The apparatus of claim 7 wherein the mouth of the elongated sleeve is fixedly attached to the lower portion.

9. An apparatus for use by a user having one hand and for use with a stethoscope having a stethoscope head with a head vertical length and a connector tube extending from the stethoscope head, wherein the connector tube has a connector tube length and a connector tube cross-sectional thickness, the apparatus comprising:
   an elongated sleeve defining an interior volume and having a closed sleeve first end and an opened sleeve second end defining a mouth having a perimeter,
      wherein the elongated sleeve is constructed of a material that is acoustically transmissive and generally impermeable to microorganisms and fluids,
      wherein the elongated sleeve has a sleeve length that falls between a first distance and a second distance, wherein the first distance is about equal to the sum of the head vertical length plus about one half of the connector tube length, and wherein the second distance is about equal to the sum of the head vertical length plus the connector tube length; and
   a clasp fixedly attached to substantially all of the perimeter of the mouth of the elongated sleeve and comprised of a resilient member formed into a generally closed-loop configuration and of sufficient size to approximately encircle the perimeter of the mouth of the elongated sleeve,
      wherein the clasp further comprises a first clasp side, a second clasp side, a first clasp end connecting the first and second clasp sides, and a second clasp end connecting the first and second clasp sides,
      wherein the clasp further comprises an upper portion having a first cross-sectional thickness and a lower portion having a second cross-sectional thickness that is less than the first cross-sectional thickness,
      wherein when no external compressive force is applied to the first and second clasp ends, the first and second clasp sides are one of abutting one another and spaced apart by a first distance that is less than the connector tube cross-sectional thickness, and
      wherein when an external compressive force is applied to the first and second clasp ends by the one hand of the user, at least a portion of the first and second clasp sides are spaced apart by a second distance that is greater than the connector tube cross-sectional thickness.

10. An apparatus for use by a user having one hand and for use with a stethoscope having a stethoscope head and a connector tube extending from the stethoscope head, wherein the stethoscope head has a head vertical length, and wherein the connector tube has a connector tube length and a connector tube cross-sectional thickness, the apparatus comprising:

an elongated sleeve defining an interior volume and having a closed sleeve first end and an opened sleeve second end defining a mouth having a perimeter, wherein the elongated sleeve is constructed of a material that is acoustically transmissive and generally impermeable to microorganisms and fluids; and a clasp fixedly attached to substantially all of the perimeter of the mouth of the elongated sleeve and comprised of a resilient member formed into a generally closed-loop configuration and of sufficient size to approximately encircle the perimeter of the mouth of the elongated sleeve, wherein the clasp further comprises an upper portion having a first cross-sectional thickness and a lower portion having a second cross-sectional thickness that is less than the first cross-sectional thickness, wherein the elongated sleeve has a sleeve length that falls between a first distance and a second distance, wherein the first distance is about equal to the sum of the head vertical length plus about one half of the connector tube length, and wherein the second distance is about equal to the sum of the head vertical length plus the connector tube length, wherein the clasp further comprises a first clasp side, a second clasp side, a first clasp end connecting the first and second clasp sides, and a second clasp end connecting the first and second clasp sides, wherein when no external compressive force is applied to the first and second clasp ends, each of the first and second clasp sides has a generally elongated shape and is one of abutting one another and spaced apart by a third distance that is less than the connector tube cross-sectional thickness, wherein when an external compressive force is applied to the first and second clasp ends by the one hand of the user, each of the first and second clasp sides has a generally arcuate shape, and at least a portion of the first and second clasp sides are spaced apart by a fourth distance that is greater than the connector tube cross-sectional thickness.

11. The apparatus of claim 10, wherein the mouth of the elongated sleeve is fixedly attached to the clasp lower portion.

12. A method of inhibiting the transmission of microorganisms, comprising:

applying an external compressive force to first and second clasp ends of a clasp using one hand, wherein the clasp is fixedly attached to an elongated sleeve, wherein the clasp further comprises a first clasp side and a second clasp side, and wherein the first clasp end connects the first and second clasp sides and the second clasp end connects the first and second clasp sides;

inserting a stethoscope head of a stethoscope and at least a portion of a connector tube of the stethoscope into the elongated sleeve while the external compressive force is being applied to the first and second clasp ends, wherein the connector tube extends from the stethoscope head; and releasing the external compressive force from the first and second clasp ends after the stethoscope head and the at least a portion of the connector tube are inserted into the elongated sleeve, wherein the elongated sleeve is constructed of a material that is acoustically transmissive and generally impermeable to microorganisms and fluids.

13. The method of claim 12 wherein the stethoscope head has a head vertical length and the connector tube has a connector tube length, wherein the elongated sleeve has a sleeve length that falls between a first distance and a second distance, wherein the first distance is about equal to the sum of the stethoscope head vertical length plus about one half of the connector tube length, and wherein the second distance is about equal to the sum of the head vertical length plus the connector tube length.

14. The method of claim 12 wherein the clasp comprises a resilient member formed into a generally closed-loop configuration and of sufficient size to approximately encircle a perimeter of a mouth of the elongated sleeve, wherein the first and second clasp sides are one of abutting one another and spaced apart by a first distance when no external compressive force is applied to the first and second clasp ends and when the stethoscope head and the at least a portion of the connector tube are not inserted into the elongated sleeve, wherein the first distance is less than a cross-sectional thickness of the connector tube, and wherein at least a portion of the first and second clasp sides are spaced apart by a second distance that is greater than the connector tube cross-sectional thickness when the external compressive force is applied to the first and second clasp ends.

15. The method of claim 12 wherein each of the first and second clasp sides has a generally elongated shape when no external compressive force is applied to the first and second clasp ends and the stethoscope is not inserted into the elongated sleeve, and wherein each of the first and second clasp sides has a generally arcuate shape when the external compressive force is applied to the first and second clasp ends.

16. A method of covering a stethoscope to protect the stethoscope from microorganisms, the method comprising:

holding a cover sleeve with one hand;

resiliently shifting opposite ends of a resilient clasp member of the cover sleeve toward each other via a compressive force exerted on the ends by the one hand to open an upper mouth opening of the cover sleeve;

inserting a head of the stethoscope and at least a portion of a connector tube of the stethoscope extending from the head through the upper mouth opening into the cover sleeve; and removing the compressive force on the resilient clasp member ends to cause opposite portions of the clasp member to grip on the stethoscope connector tube so that the cover sleeve is held on the stethoscope by the opposite portions of the clasp member in gripping engagement with the connector tube.

17. An apparatus for use by a user having one hand and for use with a stethoscope having a stethoscope head and a connector tube extending from the stethoscope head, the apparatus comprising:

means for isolating the stethoscope head and at least a portion of the stethoscope connector tube from microorganisms, wherein the isolating means is acoustically transmissive; and means for removably securing the isolating means onto the stethoscope using the one hand wherein the securing means includes a clasp configured to grip the connector tube.

* * * * *